United States Patent
Koltz, Jr.

(10) Patent No.: US 12,121,633 B2
(45) Date of Patent: Oct. 22, 2024

(54) NANODIAMOND ELECTROSURGICAL COATING

(71) Applicant: Conmed Corporation, Utica, NY (US)

(72) Inventor: Michael J. Koltz, Jr., Aurora, CO (US)

(73) Assignee: Conmed Corporation, Utica, NY (US)

( * ) Notice: Subject to any disclaimer, the term of this patent is extended or adjusted under 35 U.S.C. 154(b) by 85 days.

(21) Appl. No.: 16/940,899

(22) Filed: Jul. 28, 2020

(65) Prior Publication Data
US 2021/0030929 A1 Feb. 4, 2021

Related U.S. Application Data

(60) Provisional application No. 62/879,645, filed on Jul. 29, 2019.

(51) Int. Cl.
| | | |
|---|---|---|
| *A61L 31/10* | (2006.01) | |
| *A61L 31/12* | (2006.01) | |
| *B05D 1/18* | (2006.01) | |
| *B05D 3/02* | (2006.01) | |
| *C23C 14/06* | (2006.01) | |

(52) U.S. Cl.
CPC ............ *A61L 31/10* (2013.01); *A61L 31/126* (2013.01); *B05D 1/18* (2013.01); *B05D 3/0272* (2013.01); *C23C 14/0611* (2013.01); *A61L 2400/12* (2013.01); *A61L 2420/02* (2013.01); *A61L 2420/04* (2013.01)

(58) Field of Classification Search
CPC ......... A61L 31/10; A61L 31/126; B05D 1/18; A61B 18/14
See application file for complete search history.

(56) References Cited

U.S. PATENT DOCUMENTS

| | | | |
|---|---|---|---|
| 10,433,898 B2* | 10/2019 | Borgmeier | ......... A61B 18/1402 |
| 2013/0325004 A1* | 12/2013 | Greep | ............... A61B 18/1445 |
| | | | 606/45 |

OTHER PUBLICATIONS

R2, Diamond Blade Guide, May 2013, UKAM, pp. 1-11 (Year: 2013).*
R1, Nano Diamond Powder CAS 7782-40-3, Jun. 2019, TRUN-NANO, pp. 1-4 (Year: 2019).*

* cited by examiner

*Primary Examiner* — Dah-Wei D. Yuan
*Assistant Examiner* — Andrew J Bowman
(74) *Attorney, Agent, or Firm* — Bond, Schoeneck & King, PLLC; David L. Nocilly

(57) ABSTRACT

A coating for an electrosurgical electrode to reduce the potential for sticking of tissue. The coating is an elastomer containing a plurality of diamond particles having an average diameter of between diameter of 0.5 and 500 nanometers and that comprise between 0.1 and 25 percent by weight of the coating. The coating may be formed by reducing a silicone dispersion with xylene, adding the plurality of diamond particles, and agglomerating the plurality of diamond particles through sonification and then applied to the device. The coasting may also be formed by reducing a silicone dispersion with xylene, adding the plurality of diamond particles, and agglomerating the plurality of diamond particles through sonification, and then applied to the device by plasma enhanced vapor deposition.

4 Claims, 3 Drawing Sheets

NANODIAMOND ELECTROSURGICAL COATING

CROSS-REFERENCE TO RELATED APPLICATIONS

The present application claims priority to U.S. Provisional No. 62/879,645, filed on Jul. 29, 2019.

BACKGROUND OF THE INVENTION

1. Field of the Invention

The present invention relates to electrosurgical instruments and, more specifically, to a non-stick coating with diamond nano-particles for improved durability.

2. Description of the Related Art

Electrosurgical vessel sealers are used for the occlusion of blood vessels and halting of bleeding during surgical procedures. The electrodes of the vessel sealer are interconnected to an electrosurgical generator that can selective supply radiofrequency (RF) energy to the electrodes for the desiccation and sealing of a blood vessel that has been clamped between the electrodes. A blade may be additionally incorporated into the jaws for cutting of the sealed blood vessel along an intermediate portion of the seal created by the energized electrodes.

One problem that arises in the use of electrosurgical vessel sealers is the accumulation of eschar on the electrodes due to tissue sticking during treatment. Coatings are therefore often applied to the applied to the electrodes to prevent the adherence of tissue. These coating exhibit rapid wear, however, due to high temperatures, arc erosion, and mechanical abrasion. In fact, these coatings begin to breakdown upon the first electrical activation and continue to degrade in sticking performance upon each successive activation. A solution to the problem of coating degradation has been the use of thicker coatings. While thicker coatings are inherently more durable, the added coating thickness reduces RF energy transmission and increases variability in vessel sealing performance with respect to burst pressures. Accordingly, there is a need in the art for a coating that can resist wear without compromising the transmission of RF energy.

BRIEF SUMMARY OF THE INVENTION

The present invention is a coating for electrosurgical instruments such as vessel sealing that includes diamond nano-particles for increasing durability. The present invention allows for the use of thinner coatings that yield non-stick properties over more activation cycles with less variation in sealing performance. Additionally, the non-stick properties slow the buildup of eschar, thereby reducing the intraoperative time required to clean the electrode and thus shortening procedures.

In a first embodiment, the present invention is a coating for an electrosurgical electrode comprising an elastomer and a plurality of diamond particles embedded in the elastomer, wherein the plurality of diamond particles have an average diameter of between diameter of 0.5 and 500 nanometers. The plurality of diamond particles may have an average diameter of between 3 and 10 nanometers. The plurality of diamond particles may comprise between 0.1 and 25 percent by weight of the coating. The plurality of diamond particles may comprise ten percent by weight of the coating. The elastomer may comprise silicone.

In another embodiment, the present invention comprises a method of reducing the likelihood of tissue sticking to a medical device comprising the steps of preparing a coating containing a plurality of diamond particles and coating at least a portion of the electrosurgical device with the coating. The coating may be prepared by reducing a silicone dispersion with xylene, adding the plurality of diamond particles, and agglomerating the plurality of diamond particles through sonification. The medical device may then be coated by dipping the portion of the electrosurgical device in the silicone dispersion and then drying the portion of the electrosurgical device in an oven to evaporate the xylene. The coating may also be prepared by combining the plurality of diamond particles with a siloxane to form a vapor deposition precursor. The vapor deposition precursor may then be deposited onto the portion of the electrosurgical device using plasma enhanced vapor deposition.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
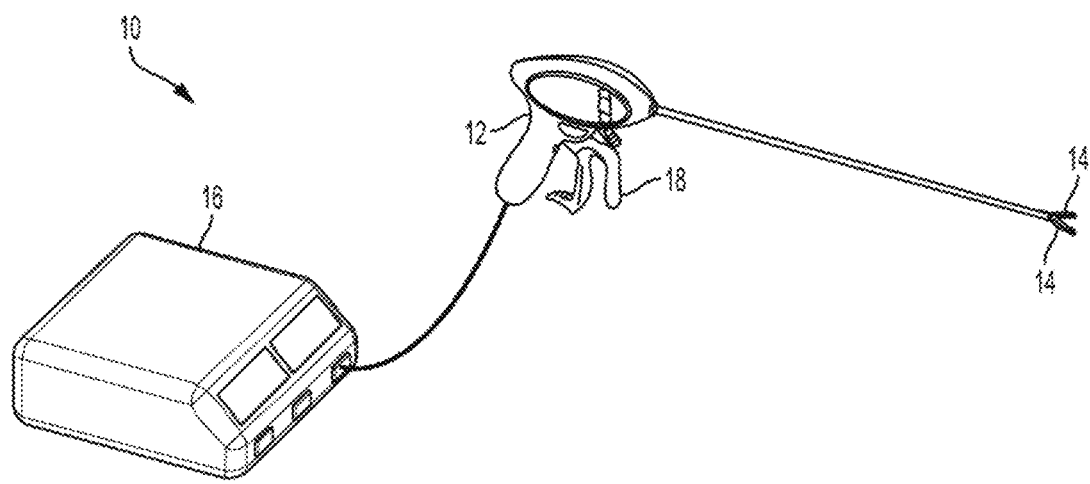
FIG. 1 is a schematic of an electrosurgical system having a pair of jaws carrying electrodes for electrosurgically treating tissue.

Referring to the figures, wherein like numeral refer to like parts throughout, there is seen in FIG. 1 a vessel sealing system 10 comprising a vessel sealer 12 having a pair of conductive opposing jaws 14 that are interconnected to an electrosurgical generator 16 that can supply RF energy to electrodes of jaws 14 for the desiccation of a blood vessel trapped between jaw 14. The dimensions of jaw 14 and the type of RF energy supplied will produce desiccation of the blood vessel in a region of a particular width as determined by the thermal spread of the energy being supplied to the blood vessel. As is known in the art, jaws 14 are pivotally mounted to vessel sealer 12 for movement between an open position and a closed position in response to a user operating a handle 18 of sealer 12.

Figure 2:
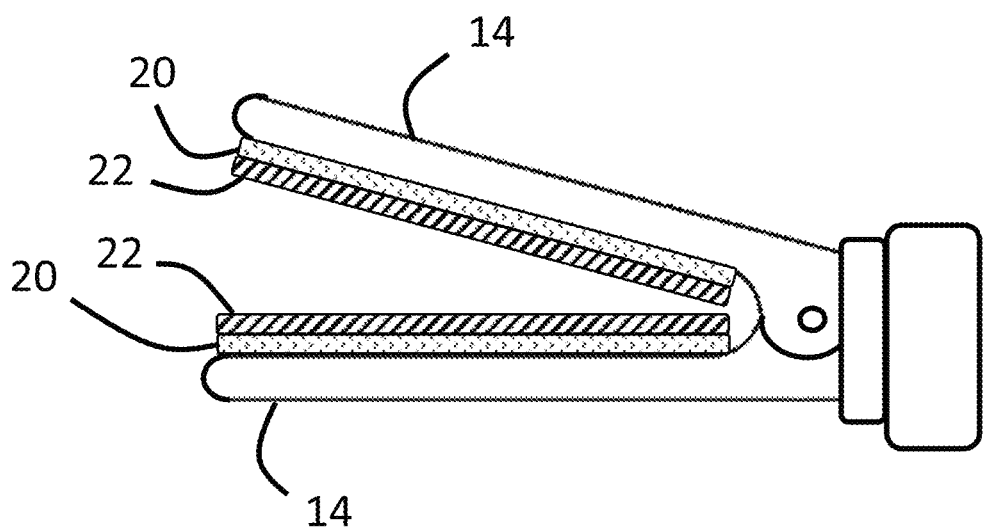
FIG. 2 is a side view of a pair of jaws of an electrosurgical vessel sealer having a coating according to the present invention applied to the electrodes of the jaws of an electrosurgical vessel sealer.

Referring to FIG. 2, jaws 14 of vessel sealer 12 carry a pair of corresponding electrodes 20. Each electrode 20 has a planar surface that is covered, at least in part, by a coating 22 according to the present invention. Coating 22 comprises a silicone matrix filled with diamond particles. The thickness of coating 22 is nominally 5 microns, but in other embodiments may range from 30 nanometers to 25 microns depending on the particular application. The diamond particles are preferably nano-sized and have an average diameter of between 3 and 10 nanometers, but in other embodiments could range in size between 0.5 and 500 nanometers. The diamond nanoparticle content in coating 22 is generally 10 percent by weight, but could range from 0.1 to 25 percent depending on the application.

At a minimum, coating 22 is applied to the conductive electrode components of vessel sealer 12. Coating 22 could additionally cover adjacent surfaces that can come into contact with the tissue of a patient, such as any of the components of jaws 14 of vessel sealer 12 regardless of the whether the components are formed from metals, polymers, or ceramics to improve non-stick properties of those surfaces and thus reduce the possibility of eschar buildup. Coating 22 may also be applied to monopolar electrodes and bipolar electrodes not specifically intended for vessel sealing.

Coating 22 is formulated using a silicone dispersion and adding diamond nano-particles prior to forming a resin. For example, coating 22 may be formed by beginning with a silicone dispersion such as a one-part room temperature vulcanizing acetoxy silicone dispersed in xylene and then reducing the viscosity of the silicone dispersion via the addition of a dispersant, such as xyleneNUSIL™ MED10-6605 available from Avantor, Inc. is an acceptable one-part RTV silicone elastomer dispersed in xylene. Diamond nano-particle powder may then be added to produce coating 22 as a resin containing diamond nano-particles. For example, diamond nano-particles with a particle size of less than 50 nm and surface area is an average of 100 m2/g are commercially available from a variety of sources. An optimal formula comprises a 2400:800:1 ratio by weight of xylene:MED10-6605:diamond of uncured material (not included any xylene in the MED10-6605). The xylene will evaporate during curing.

Agglomeration of the powder may be reduced through sonification of the resin. Electrode subassemblies consisting of metals, polymers, and ceramics may then be dipped into the resin and subsequently placed in an oven to speed the evaporation of the xylene dispersant. The diamond nano-particles may also be combined with siloxanes to form a precursor for plasma enhanced chemical vapor deposition. The deposition is completed at atmospheric pressure in some embodiments and under vacuum in others.

Figure 3:
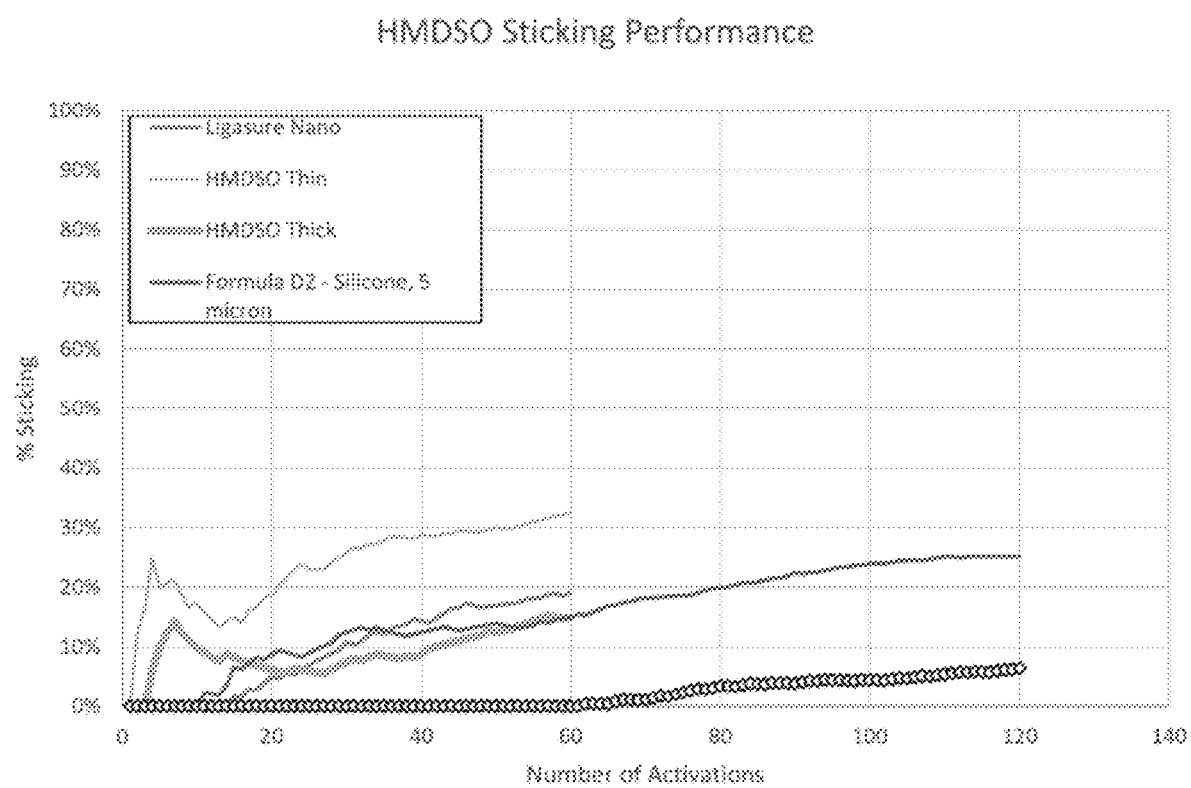
FIG. 3 is a graph of the performance of a coating according to the present invention as compared to various conventional coatings.

The addition of diamond particles to the polymeric matrix for coating 22 increases the durability of coating 22 as compared to conventional coatings and improves non-stick properties. Referring to FIG. 3, the degradation of the non-stick properties can be measured and observed to occur in less than one dozen activation cycles for conventional coatings, which coating 22 according to the present invention resist any sticking of tissue during RF treatment for over 50 activation cycles. Coating 22 exhibits increased durability for several reasons. First, the high inherent hardness of diamond particles reduces wear via mechanical abrasion. Second, the high thermal conductivity of diamond improves thermal heat sinking away from areas of electrical discharge with local high temperatures. Finally, the high dielectric strength of diamond inhibits electrical discharge and the associated dielectric breakdown of coating 22.

The coating impregnated with diamond nano-particles exhibits a combination of properties, including high hardness, high thermal conductivity, high dielectric strength, and an electrical impedance that is lower than other low surface energy polymers. The coating properties provide non-stick performance over more activation cycles than conventional electrosurgical coatings and the coating of the present invention can be applied using low-cost atmospheric application methods such as dipping.

What is claimed is:

1. An electrosurgical device having a coating for reducing tissue adhesion, comprising:
  a vessel sealer having pair of jaws;
  a pair of electrosurgical electrodes positioned in the pair of jaws, wherein each of the pair of jaws of the vessel sealer include a planar surface that will contact tissue to be treated when the pair of jaws are closed; and
  a coating including an elastomer and a plurality of diamond particles embedded in the elastomer, wherein the plurality of diamond particles have an average diameter of between diameter of 0.5 and 500 nanometers and wherein the plurality of diamond particles comprise between 0.1 and 25 percent by weight of the coating;
  wherein the coating is applied to the planar surface of each of the pair of electrosurgical electrodes so that the coating will contact any tissue trapped between the jaws when the jaws of the vessel sealer are closed; and
  wherein the coating permits radiofrequency energy to pass from the pair of electrosurgical electrodes to the tissue trapped between the jaws and prevents the tissue from sticking to the electrodes over at least fifty activation cycles.

2. The coating of claim 1, wherein the plurality of diamond particles have an average diameter of between 3 and 10 nanometers.

3. The coating of claim 1, wherein the plurality of diamond particles comprise ten percent by weight of the coating.

4. The coating of claim 3, wherein the elastomer comprises silicone.

* * * * *